(12) United States Patent
Wang et al.

(10) Patent No.: US 10,035,025 B2
(45) Date of Patent: Jul. 31, 2018

(54) CLOSE-PROXIMITY RANGE SHIFTING DEVICE FOR PROTON RADIOSURGERY

(71) Applicant: UNIVERSITY OF IOWA RESEARCH FOUNDATION, Iowa City, IA (US)

(72) Inventors: Dongxu Wang, Iowa City, IA (US); Daniel Hyer, Iowa City, IA (US); Blake Dirksen, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/301,555

(22) PCT Filed: Apr. 1, 2015

(86) PCT No.: PCT/US2015/023856
§ 371 (c)(1),
(2) Date: Oct. 3, 2016

(87) PCT Pub. No.: WO2015/153746
PCT Pub. Date: Oct. 8, 2015

(65) Prior Publication Data
US 2017/0173363 A1    Jun. 22, 2017

Related U.S. Application Data

(60) Provisional application No. 61/975,260, filed on Apr. 4, 2014.

(51) Int. Cl.
*A61N 5/10* (2006.01)
*G21K 1/10* (2006.01)
*H05H 7/12* (2006.01)

(52) U.S. Cl.
CPC ............. *A61N 5/10* (2013.01); *A61N 5/1048* (2013.01); *G21K 1/10* (2013.01);
(Continued)

(58) Field of Classification Search
CPC .................... A61N 5/10; A61N 5/1048; A61N 2005/1087; A61N 2005/1096; A61N 2005/1097; G21K 1/10; H05H 2007/105
(Continued)

(56) References Cited

U.S. PATENT DOCUMENTS

2008/0234531 A1* 9/2008 Welch ...................... A61N 5/10
                                                           600/2
2008/0269593 A1    10/2008 Weinstock
(Continued)

FOREIGN PATENT DOCUMENTS

WO    2013/124975    8/2013
WO    2015/003111    1/2015

*Primary Examiner* — Nicole Ippolito
(74) *Attorney, Agent, or Firm* — Smith, Gambrell & Russell, LLP

(57) ABSTRACT

A range shifting device configured to be placed close to a portion of a body of a patient during radiation beam treatment. The radiation beam treatment can include stereotactic radiosurgery (SRS). The range shifting device can be incorporated into an existing SRS localization system during SRS treatment. The range shifting device is configured to be placed close to the head of a patient during SRS treatment. The range shifting device is comprised of range shifting material. The range shifting device can be a range shifting helmet. The range shifting helmet can include a hollow frame including a plurality of apertures in which inserts made of range shifting material can be inserted.

19 Claims, 10 Drawing Sheets

(52) U.S. Cl.
CPC ................ *A61N 2005/1087* (2013.01); *A61N 2005/1096* (2013.01); *A61N 2005/1097* (2013.01); *H05H 2007/125* (2013.01)

(58) Field of Classification Search
USPC ...................... 250/396 R, 397, 492.1, 492.3
See application file for complete search history.

(56) References Cited

U.S. PATENT DOCUMENTS

2011/0046694 A1  2/2011  Forsell
2016/0256709 A1*  9/2016  Robar .................. A61B 6/5217

\* cited by examiner

CLOSE-PROXIMITY RANGE SHIFTING DEVICE FOR PROTON RADIOSURGERY

CLAIM OF PRIORITY

This application claims priority from U.S. Provisional Patent Application No. 61/975,260, filed on Apr. 4, 2014, which is relied upon and incorporated herein in its entirety by reference.

BACKGROUND

Stereotactic radiosurgery (SRS) is a specialized form of radiation therapy that focuses small radiation beams on precisely localized areas of the brain that are known or thought to contain diseased tissue. Current SRS systems, for example as illustrated in FIG. 1, mostly use photon beams. Photon radiation beams are delivered to the target area from many different angles with extreme accuracy. The method effectively treats abnormal areas of tissue with negligible damage to nearby healthy tissue. Photon radiation is most often used to treat pituitary adenomas, brain metastases, arteriovenous malformations, and the like. For example, the University of Iowa Hospitals and Clinics treats about one hundred fifty (150) patients each year, roughly around 10-15% of the total radiation therapy patients, using this SRS technology.

The most popular photon SRS systems are linear accelerator (Linac) based systems or GammaKnife systems. In GammaKnife radiosurgery, close to two hundred (200) tiny radiation beams from radioactive Co-60 sources are used. Comparatively, Linac radiosurgery delivers radiation from one source in multiple narrow, collimated photon beams known as arcs, with a tertiary collimator, known as a "cone." During the procedure, the patient is localized to pre-determined positions by a mechanical system with 0.3 mm accuracy.

Patients undergoing SRS through current methods (e.g., Linac and GammaKnife systems) are first fitted with a head ring or head frame 10, as shown in FIG. 2. The head frame 10 attaches to the head of the patient via pins/screws at various points. The head frame 10 must be tightly secured to the skull of the patient in order to establish a rigid relationship between the head and head frame 10 for the duration of the treatment. The head frame 10, along with a localization box (not shown) used during computed tomography (CT) imaging is used to establish a precise, three-dimensional coordinate system of the patient's brain. Later, when the patient is secured to the treatment table or floor stand through this head frame 10, the brain lesion can be precisely positioned at the desired location relative to the Linac beam.

While photon beams are proven for treating small, relatively uniformly shaped brain lesions, the risk of side effects increases when photon beams are used to treat large, irregularly shaped targets. Therefore, the photon SRS techniques described above becomes impractical for large target volumes.

Proton radiation, due to proton beams superior depth dose properties, has an inherent advantage in treating large, irregularly shaped lesions in comparison to photon radiation. A proton naturally releases the vast majority of its energy in matter near the end of its path, illustrated in FIG. 3, called the Bragg Peak. By manipulating proton energies, the Bragg Peak can be placed within the target volume, maximizing tumor dose but minimizing healthy tissue dose, in contrast to photons (shown along the x-ray deposition curve) that have substantial entrance and exit doses, as illustrated in FIG. 4. An advantage of proton therapy is the minimal entrance dose and virtually absent exit dose when the Bragg peak is placed at tumor.

However, placing the Bragg peaks within the tumor of various depths requires the ability to adjust proton energy. Current medical proton systems have a lower energy threshold of approximately 70 MeV, which is too high for direct treatment of shallow lesions located less than four centimeters beneath the skin, which make up a large percentage of brain lesions. In fact, the average adult human head is about sixteen centimeters wide, and the shallowest four centimeters consists of more than 50% of the brain volume where lesions may occur. For example, between May 2009 and September 2009, 25% of brain SRS patients treated at University of Iowa Hospitals and Clinics had a portion of their lesions within 3 mm of the inner skull. In addition, the shallowest four (4) centimeters of the brain is the site of many capillaries where metastasized tumors are often found due to the capillaries decreased diameter, increasing the difficulty of the tumors to flow through capillaries.

In order to treat shallow tumors and manipulate the depth at which the Bragg peak is placed, a range-shifting device is needed to lower the proton beam energy when entering the patient. It is estimated that one-third of all proton therapy procedures will require a range-shifting device, often called a range shifter. Therefore, a range shifter is necessary to treat these lesions in proton SRS.

However, existing range shifters are slabs of tissue-mimicking plastic that are often placed in the beam-line/beam exit window well above the head of a patient. Such placement leaves a considerable distance, as large as forty (40) cm, between the range shifter and the patient skin. Such distances increase the amount of lateral growth of the proton beam due to multiple Coulomb scattering inside of the range shifter. Multiple coulomb scattering refers to the gradual spread of the angular distribution of protons that arises from thousands of small electrostatic deflections by atomic nuclei. A large air gap between range shifter and patient increases the unwanted radiation dose to patient, and more specifically healthy tissue surrounding the targeted lesion, and decreases the dosimetric advantage of proton SRS. For example, FIGS. 5A-B show a simulation study that compared the radiation dose distribution applied to a tumor (outlined in yellow) for a range shifter five (5) cm away from patient head (FIG. 5A) and one range shifter forty (40) cm away from patient head (FIG. 5B). FIG. 5B shows that when a range shifter is far away from the head of a patient, a good portion of the radiation dose is delivered to healthy brain tissues outside the tumor, whereas FIG. 5A shows the radiation dose more focused around the tumor. Further, as shown in FIG. 6, there are times when proton beams are actually worse than photon beams for brain SRS application. For example, when proton beams have a lateral size of 7.1 mm or larger, proton beams may be more damaging than photon beams. In fact, proton SRS may only be superior to photon SRS when lateral size of proton beam is smaller than 4.3 mm.

Therefore, there is a need for a range shifter device that allows for the range shifting necessary in proton SRS for shallow lesions while minimizing the lateral growth of the proton beam due to scatter.

SUMMARY OF THE INVENTION

The present invention is aimed at a range shifting device configured to be placed close to a portion of a body of a patient during radiation beam treatment. In an aspect, the radiation beam treatment can include stereotactic radiosurgery (SRS). In an aspect, the range shifting device can be incorporated into an existing SRS localization system during SRS treatment. In an exemplary aspect, the present invention is aimed at a range shifting device configured to be placed close to the head of a patient during SRS, and will be very close to the patient's head for proton SRS treatment. In an aspect, the range shifting device is comprised of range shifting material.

In an aspect, the range shifting device can be a range shifting helmet. The range shifting helmet can be configured to be shaped like a hemispherical dome to be placed on the head of the patient. In another aspect, the range shifting device can include a hollow frame including a plurality of apertures in which inserts made of range shifting material can be inserted. In an exemplary aspect, the range shifting material of the range shifting device can have a thickness of approximately four (4) cm. In such aspects, the range shifting device is configured to be within five (5) cm of the patient skin, thereby minimizing the amount of lateral beam size expansion.

In an aspect, the range shifting device can be configured to attach to a head frame. In an aspect, the range shifting device can be configured to be attached to an SRS head frame configured for use during imaging and treatment of patient, and can be detached when not needed. In an aspect, the range shifting device can include an attachment mechanism configured to create a secure attachment to the head frame and minimize spatial displacement.

In an aspect, the range shifting device is used for radiation beam treatment of a shallow target within a portion of a body of a patient. In such aspects, the range shifting devices includes range shifting material that is positioned proximate an outer surface of the portion of the body of the patient to reduce the distance between an entry point and the range shifting material. In an aspect, the range shifting material is configured to lower energy of the radiation beam treatment to accommodate Bragg Peak conditions for the shallow target, as well as having high proton stopping power. In an aspect, the range shifting material can have a low atomic number to reduce scattering power of the radiation beam treatment. In an aspect, the range shifting material employed by the range shifting device is configured to have a thickness that ensure that the radiation beam treatment includes a minimal entrance dose and a virtually absent exit dose for the shallow target.

These and other objects and advantages of the invention will become apparent from the following detailed description of the preferred embodiment of the invention.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE EMBODIMENTS

Figure 1:
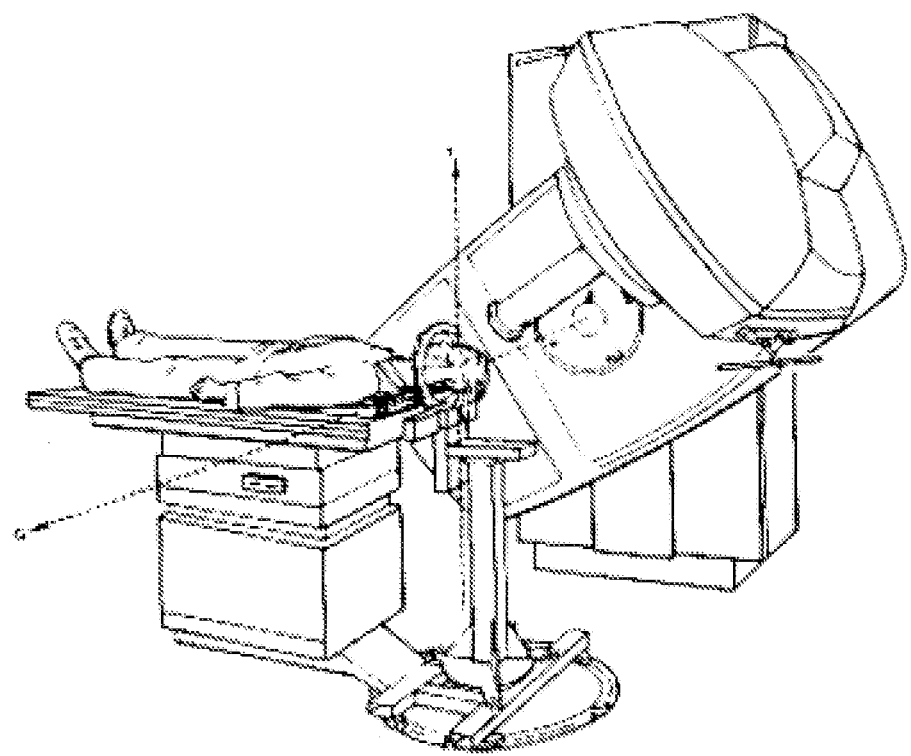
FIG. 1 illustrates an example of a standard SRS system with linear particle accelerator and robotized position table according to the prior art.
Figure 2:
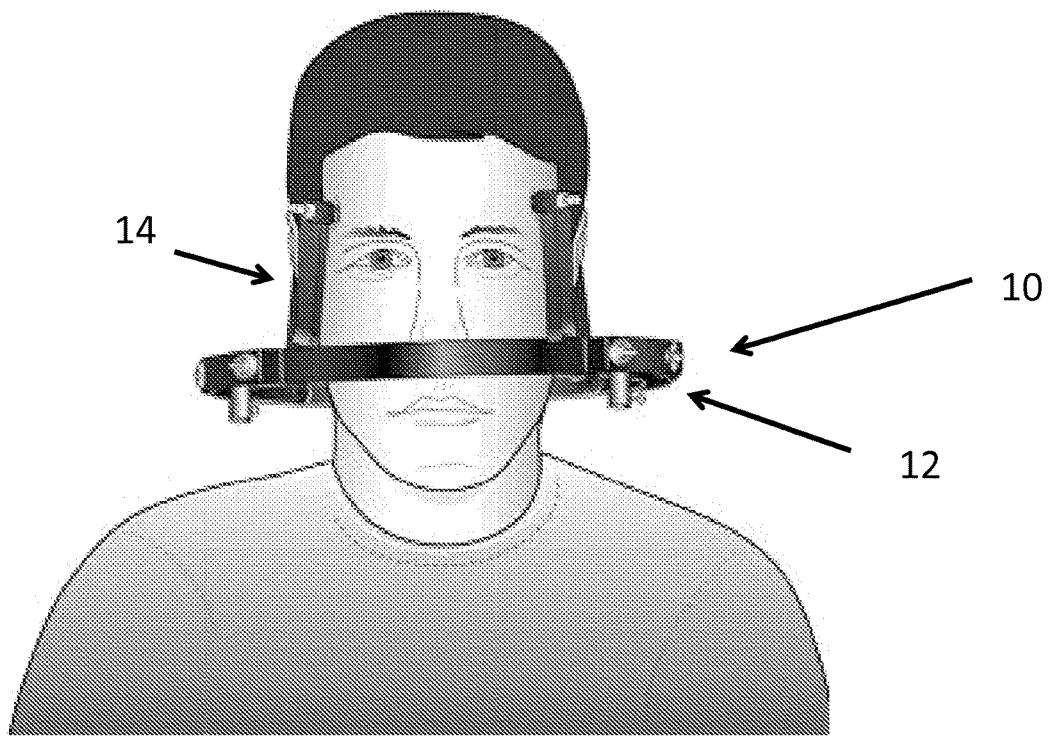
FIG. 2 illustrates a schematic of a typical head frame attached to a patient during stereotactic radiosurgery known in the art.
Figure 3:
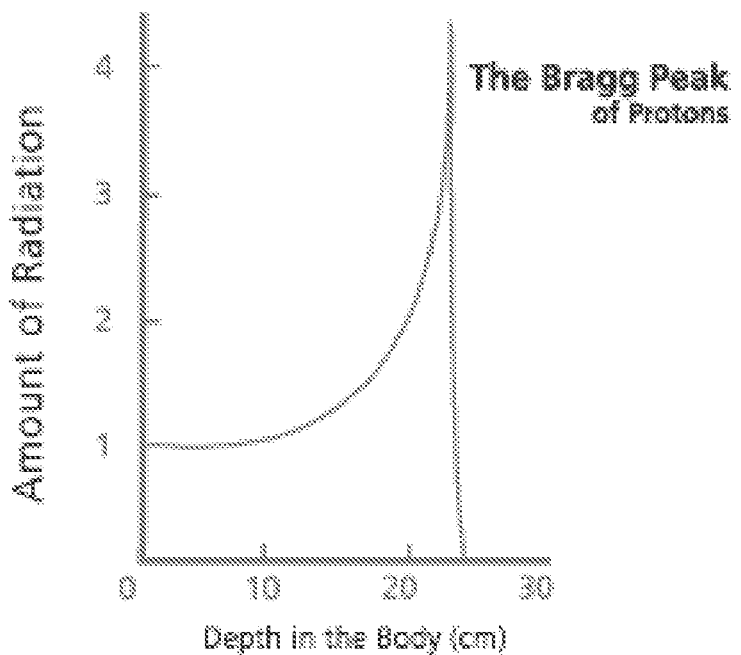
FIG. 3 is a graphical representation of the amount of radiation released by a proton within the depth of a patient's body known as the Bragg Peak.
Figure 4:
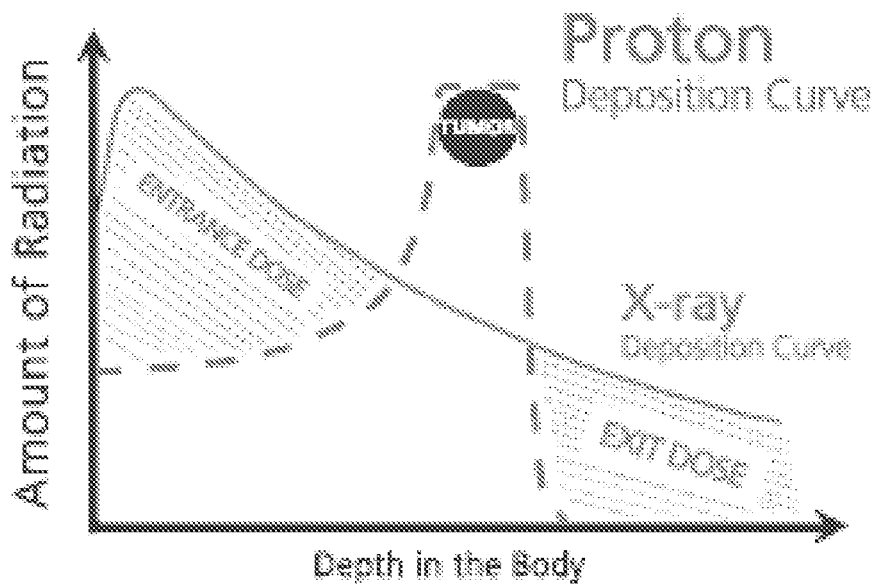
FIG. 4 is a graphical representation of the amount of radiation released by a proton and a photon (x-ray) to a tumor location within a patient's body.
Figure 5A:
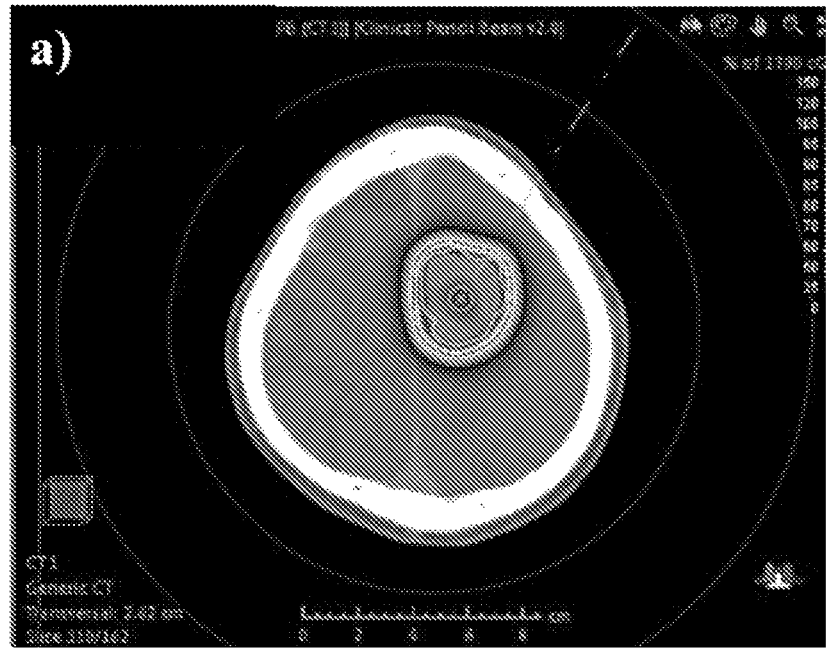
FIG. 5A illustrates the radiation dose of a proton passing through a range shifting device located five (5) cm from the head of the patient.
Figure 5B:
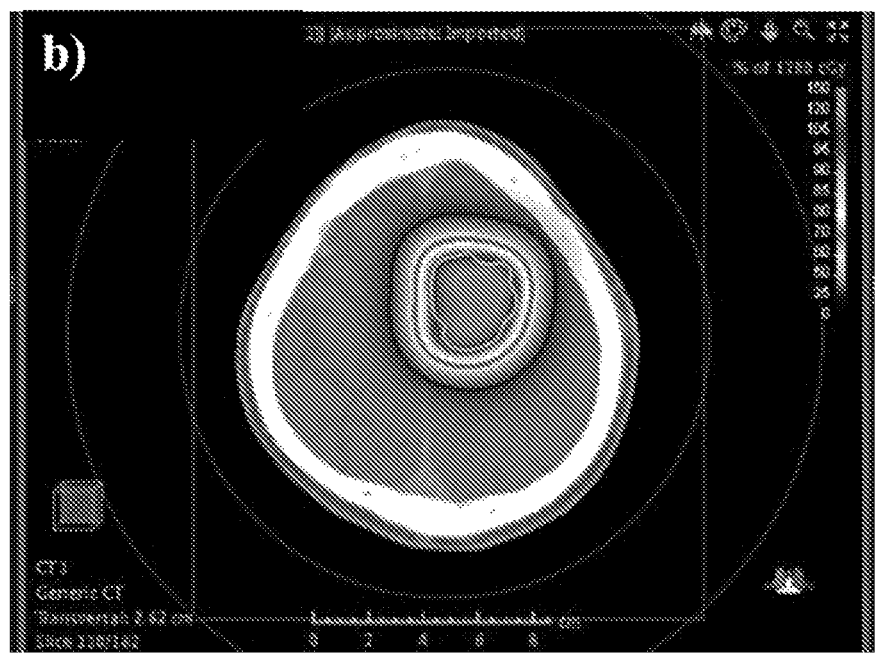
FIG. 5B illustrates the radiation dose of a proton passing through a range shifting device located forty (40) cm from the head of the patient.
Figure 6:
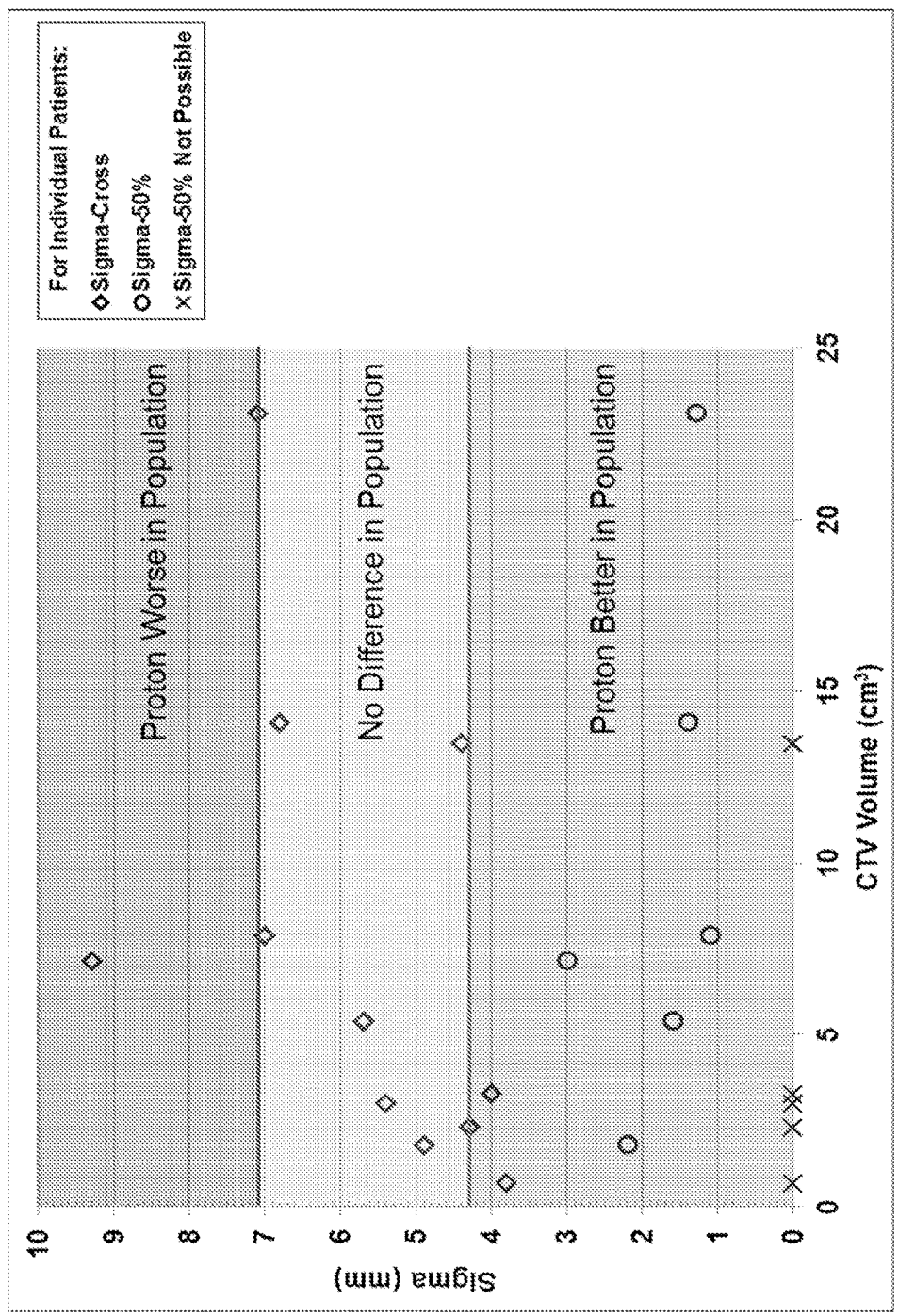
FIG. 6 is a graphical representation of the CTV Volume of the radiation exposure for patients based upon the lateral proton beam size (sigma) needed to be equal to or better than photon for SRS of peripheral brain lesions.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to an "outer-inner race", or "bearing element" can include two or more such elements unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about" it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods. References will now be made in detail to the present preferred aspects of the invention, examples of which are illustrated in the accompanying drawings.

As illustrated in FIGS. 7-14, the current invention is directed to a SRS range shifting device 20 for use in SRS treatment of areas within a patient's head. The SRS range shifting device 20 can be configured to allow close-proximity range shifting during SRS treatment. In an exemplary aspect, the SRS range shifting device 20 is configured for use in proton SRS treatment. In other aspects, the SRS range shifting device 20 can be used in carbon ion or any other heavy particle radiation. The SRS range shifting device 20 is configured to reduce the distance between the SRS range shifting device 20 and the actual skin entry point of the beam used in SRS treatment, thereby reducing lateral growth of the beam due to scattering, ultimately reducing the side effect risk. In an exemplary aspect, the SRS range shifting device 20 is specifically configured to reduce the lateral growth of a proton beam. In other aspects, the SRS range shifting device 20 can be configured for use with other forms of SRS treatment.

Figure 7:
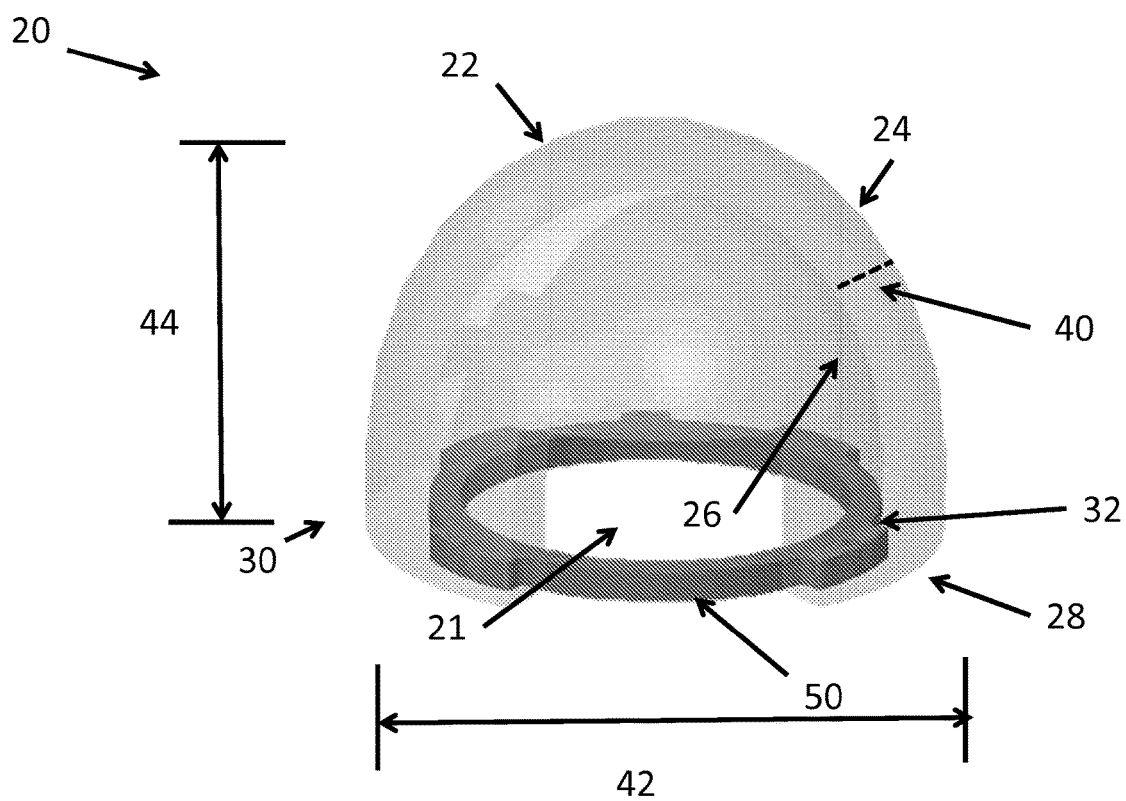
FIG. 7 is a schematic see-through representation of a range shifting device according to an aspect.
Figure 9:
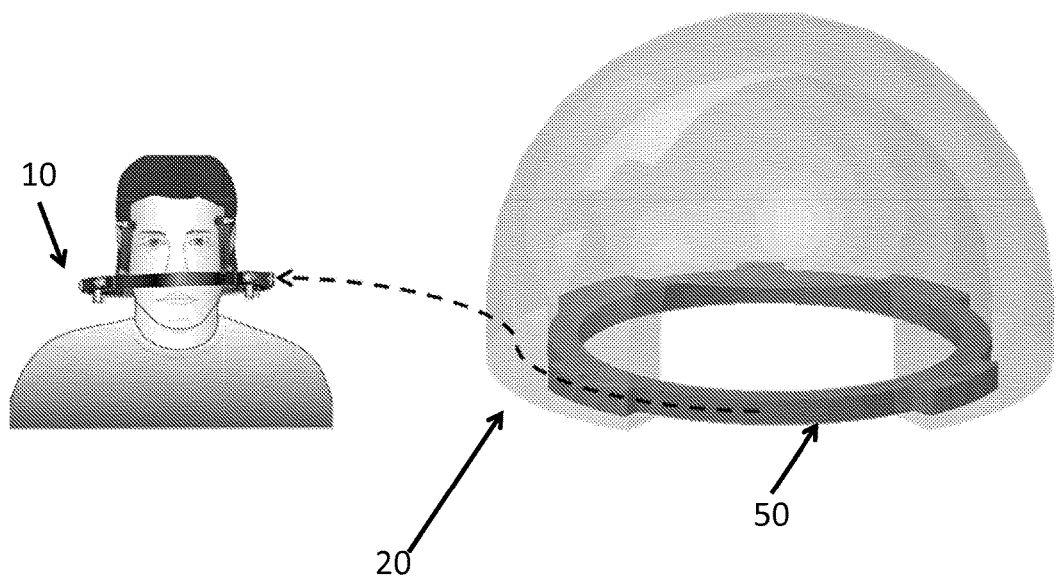
FIG. 9 is a representation of the range shifting device of FIG. 7 configured to attach to a head frame according to an aspect.
Figure 10:
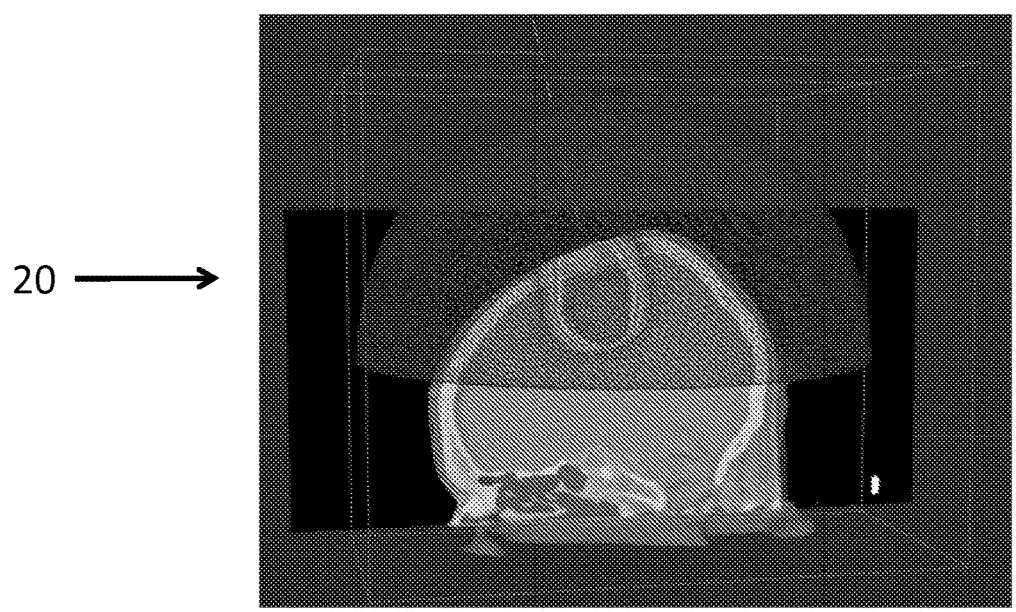
FIG. 10 is a schematic three dimensional representation of the range shifting device of FIG. 7 mounted on a head of a patient.

In an aspect, the SRS range shifting device 20 can comprise a range shifting helmet 20, as shown in FIGS. 7 and 9-10. In an aspect, the range shifting helmet 20 can be configured to be shaped like a dome or helmet to be placed on the head of the patient. In an exemplary aspect, the range shifting helmet 20 is configured to have a hemispherical dome 22, with an outer surface 24, an inner surface 26, and a bottom 28. The helmet 20 can also include an opening 21 for the face of the patient. In an aspect, the bottom 28 of the range shifting helmet 20 can include a cylindrical extension 30. In an aspect, the cylindrical extension 30 can be configured to engage a head frame 10, as well as provide range shifting for the lower back of a head. In an exemplary aspect, the cylindrical extension 30 of the range shifting helmet 20 can have a length of two (2) inches. Since most head frames 10 are at a fixed height, near the level of the nose, and the distance between eyes and the nose is about two inches, a two inch length of the cylindrical extension 30 allows the opening 21 to be aligned with the eyes of the patient once the range shifting helmet 20 is mounted on a head frame 10. However, in other aspects, the cylindrical extension 30 can vary dependent on the normal patient use (e.g., infant and children have smaller heads, leading to overall smaller range shifting helmets 20 with smaller lengths of the cylindrical extension 30).

Additional function of the cylindrical extension 30 is discussed in detail below.

In an aspect, the range shifting helmet 20 can be formed from a single piece, as shown in FIGS. 7 and 9-10. In other aspects, the range shifting helmet can be formed from more than one component. The range shifting helmet 20 can be formed from a variety of different range shifting materials. Such range shifting materials can include, but or not limited to, carbon fiber, acrylonitrile butadiene styrene, water-equivalent materials (e.g., Solid Water® from Gammex) or tissue-mimicking materials, (e.g., PMMA), graphite, acrylics, and the like. In an exemplary aspect, it is desired that the material have a density configured to have high proton stopping power while having a low atomic number to reduce the scattering power of the beam. In another aspect, the material can have an effective atomic number close to seven (7), which is the effective atomic number of water. In an aspect, the optimal material would be a balance between radiological properties, mechanical properties, and economic costs.

In an aspect, the range shifting helmet 20 can be configured to have a thickness 40. In an aspect, the thickness 40 of the range shifting helmet 20 is configured to ensure that the proton beam includes a minimal entrance dose and virtually absent exit dose at the targeted location. Therefore, the thickness 40 of the range shifting helmet 20 can be dependent on the proton energy range of the particular proton accelerator utilized. For example, when a proton accelerator having a seventy (70) MeV minimum energy threshold is used, the range shifting helmet can be configured to have a thickness of approximately four (4) cm, which is a desirable distance to ensure that the Bragg Peak of the proton can be placed within the target volume, maximizing the tumor dose while minimizing doses to healthy tissue. In another aspect, for use with a proton accelerator having a hundred (100) MeV minimum energy threshold, the thickness 40 of the range shifting helmet can be seven (7) cm.

In an aspect, the thickness 40 of the range shifting helmet 20 can be uniform. In other aspects, the thickness 40 of the range shifting helmet 20 can vary. However, in an exemplary aspect, the thickness 40 of the range shifting helmet 20 is uniform, creating a uniform distance of radiation delivery by the proton to the targeted portion of the head of the patient, and more specifically the brain. Most adult human heads are all of similar sizes, and therefore a range shifting helmet 20 can come in a uniform size in order to fit the majority of the patient population. In an exemplary aspect, the range shifting helmet 20 has an outer diameter 42 of approximately thirty-three (33) cm and a height 44 (from the top to the bottom) of approximately twenty (20) cm. Such dimensions allow a fit with most adult heads, as well as a fitting on standard head frames. However, in other aspects, customization to the range shifting helmet 20 can be made for specific needs. In an aspect, the range shifting helmets 20 can come in a wide range of different dimensions in order to more specifically fit the needs of the patients.

As discussed above, the range shifting helmet 20 is configured to engage a head frame 10. Such head frames 10 are known in the art, and are used with localization systems, such as a Linac SRS localization system (see FIG. 1), stereotactic neurosurgery and the like. However, the range shifting helmet 20 can be configured to fit various other designs of head frames. The range shifting helmet 20 can be configured to fit precisely over and around portions of the head frame 10. For example, the head frame 10 can include engaging supports 12 utilized to connect/engage with the head of the patient through known means. The engaging supports 12 of the head frame 10 must be tightly secured to the skull in order to establish a rigid relationship between the head and head frame 10 for the duration of the treatment. The engaging supports 12 are configured to support a base 14 as well. The base 14 of the head frame is configured to engage with localization systems, the range shifting helmet, and the like. As illustrated by the aspects shown in FIGS. 7 and 9-10, the range shifting helmet 20 is configured to engage a circular base 14 of the head frame 10. However, in other embodiments, the range shifting helmet 20 can be configured to engage bases 14 having other shapes.

In an aspect, the cylindrical extension 30 of the range shifting helmet 20 can include a recessed portion 32 configured to engage and retain the base 14 of the head frame 10, while the interior, or inner surface 26, of the range shifting helmet 20 surrounds the engaging supports 12, as shown in FIGS. 7 and 9. In an aspect, the recessed portion 32 can further retain an attachment mechanism 50 configured to engage the range shifting helmet 20 with the base 14 of the head frame 10. The attachment mechanism 50 is configured to securely attach the range shifting helmet 20 to the head frame 10 while minimizing spatial displacement. In an aspect, the attachment mechanism 50 can be configured to connect a localization box to the base 14 of the head frame 10 as well. In an aspect, the attachment mechanism 50 can be comprised of a metallic material. In such aspects, the use of a metallic material with the attachment mechanism 50 creates a metal-metal interface between the range shifting helmet 20 and the head frame 10, allowing the material of the range shifting helmet 20 to avoid unnecessary wear and tear.

Figure 8:
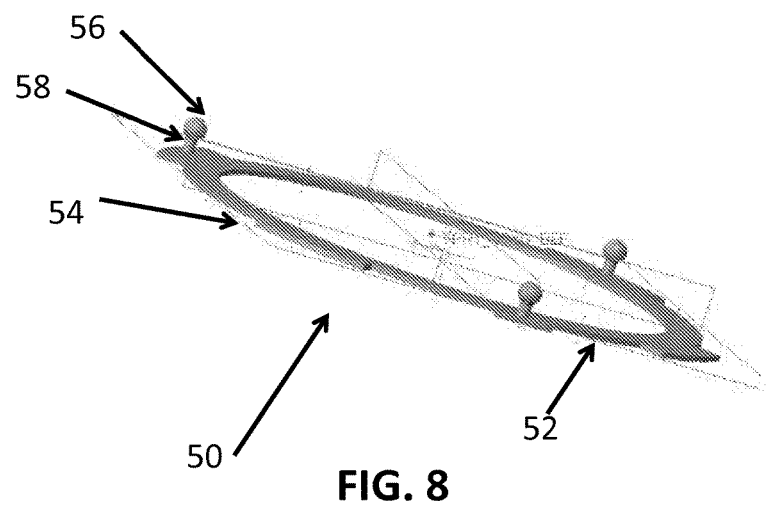
FIG. 8 is a perspective top view of an attachment mechanism of the range shifting device according to an aspect.

In an aspect, as illustrated in FIG. 8, the attachment mechanism 50 can comprise a connector ring 52. The connector ring 52 can be configured to engage with the recessed portion 32 of the range shifting helmet 20 and the base 14 of the head frame 10. In an aspect, the connector ring 52 can be secured within the recessed portion 32 of the range shifting helmet 20. The connector ring 52 can be secured to the range shifting helmet 20 through various fasteners, adhesives, and the like. The connector ring 52 can also include tabs 54 configured to engage the base 14 of the head frame 10. In an exemplary aspect, the shape and pattern of the recessed portion 32 of the range shifting helmet 20 can be configured to correspond to the shape of the connector ring 52, including the tabs 54. In an aspect, the connector ring 52 of the attachment mechanism 50 and the head frame 10 can utilize a ball and socket configuration to attach the range shifting helmet 20 to the head frame 10, as illustrated in FIG. 8. As shown in FIG. 8, multiple balls 56 can extend from the connector ring 52 on stems 58, with corresponding sockets 16 found within the base 14 of the head frame 10. In other aspects, the balls may be found on the base 14 of the head frame 10, with the sockets found within the recessed portion 32 of the range shifting helmet 20, passing through apertures found within the connecter ring 52.

In an aspect, the use of the head frame 10 allows for quick and easy transitions between a localization process and proton beam treatment. The head frame 10, along with a localization box used during computed tomography (CT) imaging, is used to establish a precise, three-dimensional coordinate system of the patient's brain, as well as for treatment. Later, when the patient is secured to the treatment table or floor stand through this head frame 10, the brain lesion can be precisely positioned at the desired location relative to the radiation beam, and the range shifting helmet 20 can be secured for use in the proton SRS treatment.

Figure 12:
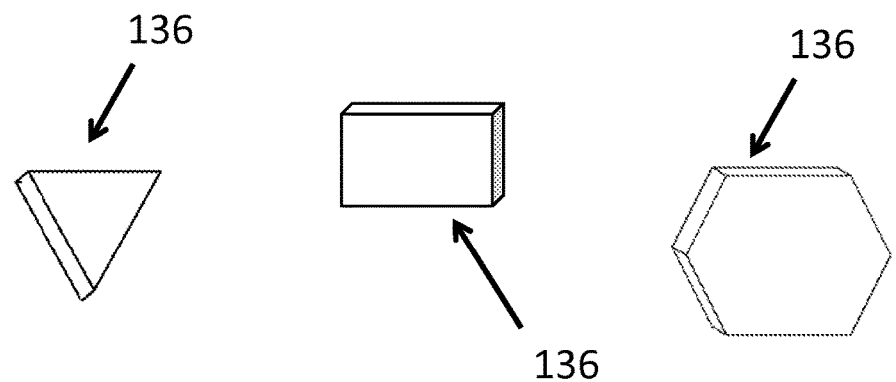
FIG. 12 is a schematic representation of inserts used with the range shifting devices of FIG. 11.
Figure 11:
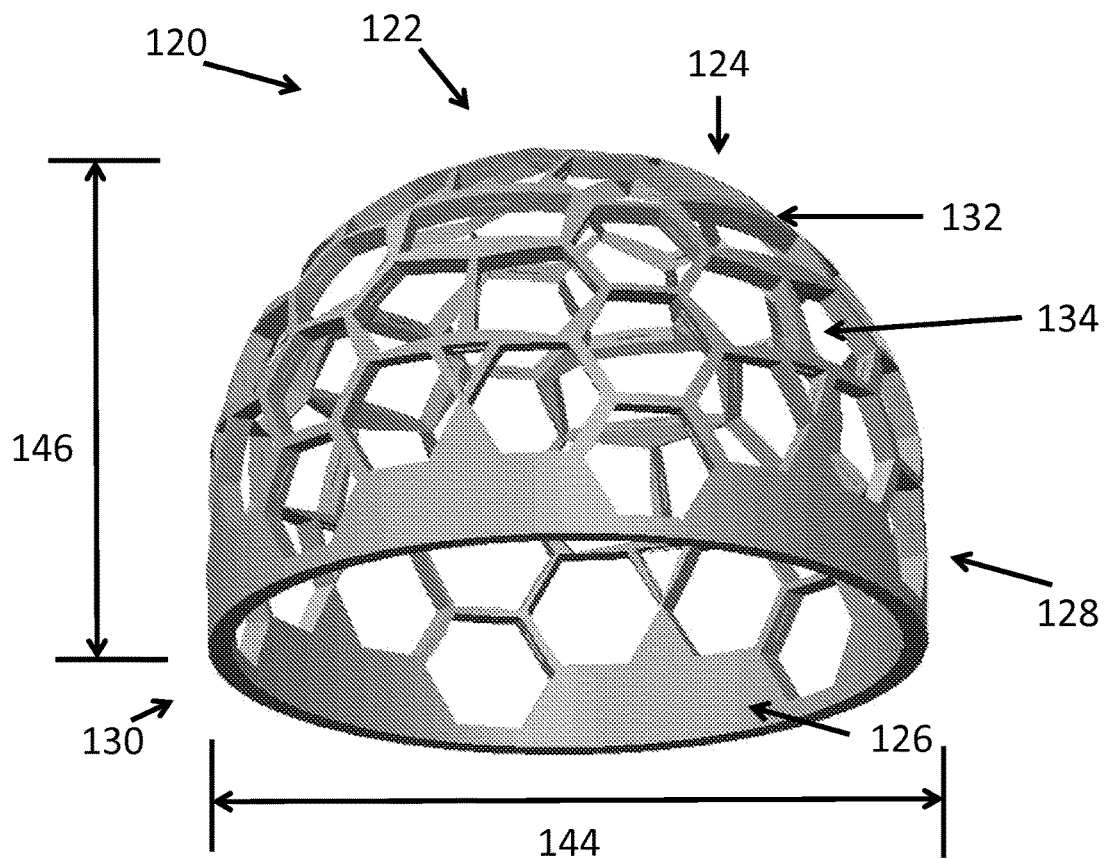
FIG. 11 is a schematic representation of a range shifting device according to an aspect.

In another aspect, as shown in FIGS. 11-12, the range shifting device 120 can comprise a hemispherical dome 122 with an outer surface 124, an inner surface 126, a bottom 128, and a cylindrical extension 130 similar to those elements discussed above in relation to FIGS. 7 and 9-10. In an aspect, the hemispherical dome 122 further comprises a hollow frame 132. The hollow frame 132 can include multiple apertures or slots 134 that are configured to retain inserts or slabs 136. The hollow frame 132 can also have the same outer diameters 144, heights 146, and thicknesses of the range shifting device 20 as discussed above. Likewise, the hollow frame 132 can be configured to engage with the head frame 10 in the same manners as discussed above, including the use of the attachment mechanism 50.

The inserts 136 are configured to be adjustable and movable within the multiple apertures 134 of the hollow frame 132 of the range shifting device 120. The inserts 136 can be secured within the apertures 134 through various securing means. Such securing means can include, but are not limited to, groove and tab configurations (groove being on the side walls of the insert 136, grooves found on the interior walls of the apertures 134, and vice versa), removable fasteners, clamps, and the like. In an aspect, the inserts 136 can be placed and secured within the apertures 134 of the hollow frame 132 based upon the location of the targeted lesion. Further, inserts 136 can be placed within the apertures 134 in an as-needed basis. More specifically, the insert(s) 136 will be placed in the particular aperture(s) 134 through which the proton beam will be aimed for treatment of the patient, which in turn depends on the location and the size of the tumor within the patient. Therefore, the apertures 136 that are not approximate the targeted area for treatment can remain empty.

In an aspect, the range shifting device 120 can include multiple apertures 134 and inserts 136 of different sizes and shapes. For example, as illustrated in FIGS. 11-12, the range shifting device 120 can include, but is not limited to, rectangular, triangular, and hexagonal apertures 134 and inserts 136, as well as other various shapes. No matter the shape, the size and shapes of the apertures 134 need to correspond to the size and shape of a matching insert 136. In an aspect, the inserts 136 can be comprised of the same materials utilized by the range shifting helmet 20 discussed above, as well as the same range of thicknesses.

By utilizing adjustable/movable inserts 136 as opposed to a single piece, full size range shifting helmet 20 as discussed above, the overall weight of the range shifting device 120 is decreased. In an aspect, the hollow frame 132 can have a smaller thickness than that of the thickness of the inserts 136, since the proton beam is being directed through the inserts 136 and not the frame 132, which allows the range shifting device 120 to be even lighter. In some aspects, the hollow frame 132 can be made from a different material than the inserts 136. The material utilized by the hollow frame 132 can have different properties than that of the material of the inserts 136. For example, the hollow frame 132 can be made of a lighter material than the inserts 136, which reduces the overall weight of the range shifting device 120 even further. In an aspect, it is desirable for the hollow frame 136 to comprise range shifting materials as well. In an exemplary aspect, the hollow frame 132 may comprise, but is not limited to, acrylic, carbon fiber, PMMA, and the like, while the inserts are made from graphite and heavier materials. In addition, the hollow frame 132 can be made of a more rigid and durable material than the inserts 136, allowing the frame 132 to last longer; the inserts 136, being smaller than that of the hollow frame 132, can be easier and cheaper to replace/repair after radiation or mechanical damage. In addition, the hollow frame 132 lessens the amount that the patient is isolated from his or her surrounding areas via the unused apertures 134, which can improve the overall comfort of the patient. In some aspects, the hollow frame 132 can comprise non-range shifting material. In such aspects, the radiation beam treatment should be oriented in such a manner as to prevent the radiation beam from engaging with the non-range shifting material of the hollow frame 132. If the radiation beam treatment needs to travel through portions of the hollow frame 132, the hollow frame 132 should avoid materials with high atomic numbers as such materials will create artifacts in the treatment planning images.

Figure 13:
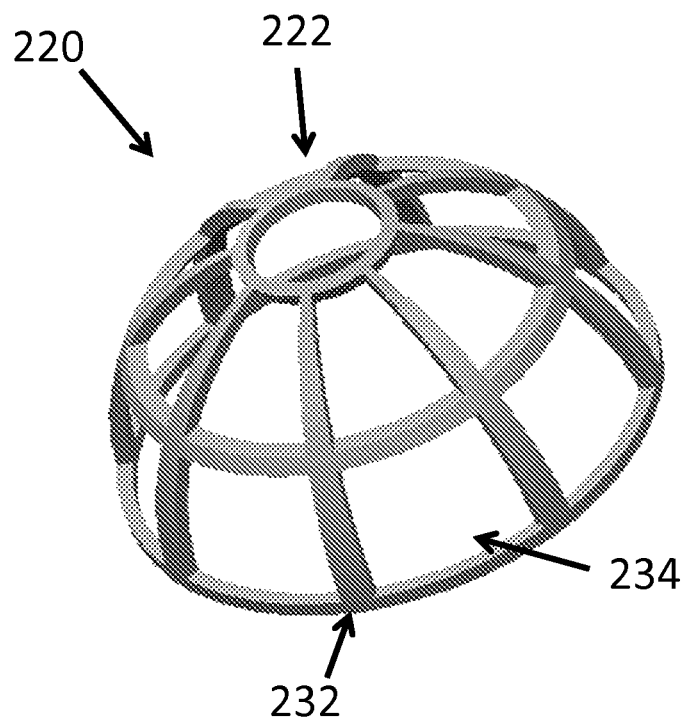
FIG. 13 is a schematic representation of a range shifting device according to an aspect.
Figure 14:
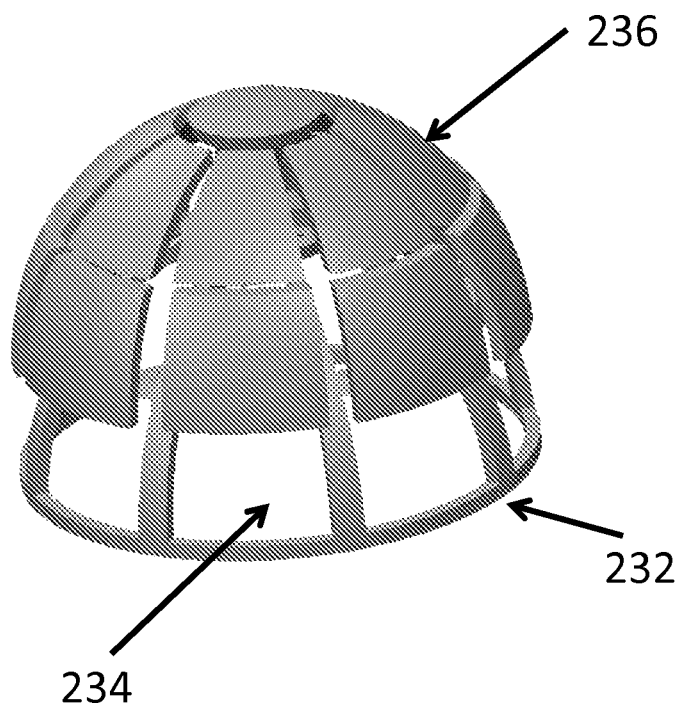
FIG. 14 is a schematic representation of the range shifting device of FIG. 13 with inserts.

FIGS. 13-14 illustrate another range shifting device 220 according to another aspect. The range shifting device 220 can comprise a hemispherical dome 222 with a cylindrical extension, and additional elements discussed above in relation to FIGS. 7 and 9-12. In an aspect, the hemispherical dome 222 further comprises a hollow frame 232, with multiple apertures 234 and inserts 236, similar to the range shifting device 120 shown in FIGS. 11-12. The inserts 236 are configured to be adjustable and movable within the multiple apertures 234 of the hollow frame 232 of the range shifting device 220. The inserts 236 can be secured within the apertures 234 through various securing means, including, but not limited to, groove and tab configurations, removable fasteners, clamps, and the like. In an aspect, the inserts 236 can be placed and secured within the apertures 234 of the hollow frame 232 based upon the location of the targeted lesion in an as-needed basis.

In an aspect, the range shifting device 220 can include multiple apertures 234 and inserts 236 of three different shapes. For example, as illustrated in FIG. 14, the range shifting device 220 can include, but is not limited to, curvilinear circle, trapezoidal, and rectangular curvilinear apertures 234 and inserts 236.

The embodiments and aspects of the range shifting devices 20, 120, 220 discussed above provide many advantages for proton SRS treatment. First, the range shifting devices are configured to lower the energy of the radiation beam, i.e. range-shift, to accommodate Bragg Peak conditions for shallow lesions within the brain, especially those lesions at depths less than four (4) cm deep when a seventy (70) MeV proton accelerator is utilized. This allows the application of current proton therapy devices, which have energy levels greater than seventy (70) MeV, to be used to treat lesions shallower than four (4) cm below skin.

Second, by attaching the range shifting devices 20, 120, 220 directly to the head frame 10, the range shifting devices 20, 120, 220 can be kept within close proximity of an adult human head (in the exemplary aspect discussed above, roughly within five (5) centimeters), reducing the lateral growth of proton beam size due to scattering.

Third, by being configured to use the head frame systems 10 utilized in other well established procedures, the range shifting devices 20, 120, 220 adhere to the tried and true Linac SRS localization systems that can be relatively easily brought to proton SRS. The range shifting devices, in either the solid range shifting helmet 20 or hollow frame range shifting helmets 120 and 220, can be modeled to fit over the head frame system 10 with a high reproducibility and accuracy in order to keep spatial movement of the SRS system as low as possible once attached. There are two features that will minimize the spatial movement of the proposed range-shifting helmets 20, 120, 220. By utilizing the localization box mounting points on the head frame 10, the range shifting devices 20, 120, 220 can be posited very accurately. In an aspect, the use of the range shifting devices 20, 120, 220 with the already established and used head frame 10 can ensure that spatial displacement from original positioning does not exceed 0.3 mm.

Further, the features described above are adaptable and easy to use for current physicians who are familiar with head frame systems in stereotactic radiosurgery or neurosurgery. The design of the range shifting devices 20, 120, 220 as a single piece range shifting helmet 20 or movable inserts 136, 236 of the hollow frame2 132, 232, is not cumbersome and provides complete coverage of possible proton beam delivery angles. In addition, the attachment mechanism 50 can be the same that is used to connect the 3D imaging localization box to the head frame in Linac SRS. The range shifting device and the 3D imaging localization box can be two interchangeable attachments for the head frame. This way, the range-shifting device may be attached quickly and efficiently with little effort by the clinical team in the radiosurgery process. In addition, the range shifting device can be configured for use with localization purposes, removing the need of a separate localization box entirely.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein.

What is claimed is:

1. A range shifting device for use in radiation beam treatment of a shallow target within a portion of a head of a patient, wherein the range shifting device comprises:
   a helmet comprising range shifting material, the helmet configured to be placed within close proximity of an outer surface of the head of the patient to reduce the distance between an entry point and the range shifting material.

2. The range shifting device of claim 1, wherein the range shifting material is further configured to lower energy of the radiation beam treatment to accommodate Bragg Peak conditions for the shallow target.

3. The range shifting device of claim 1, wherein the range shifting material has a density configured to have high proton stopping power.

4. The range shifting device of claim 3, wherein the range shifting material has a low atomic number to reduce scattering power of the radiation beam treatment.

5. The range shifting device of claim 3, wherein the range shifting material comprises a tissue mimicking material.

6. The range shifting device of claim 3, wherein the range shifting material has an effective atomic number of seven.

7. The range shifting device of claim 1, wherein the range shifting material is configured to have a thickness that ensures the radiation beam treatment includes a minimal entrance dose and virtually absent exit dose at the shallow target.

8. The range shifting device of claim 7, wherein the thickness is approximately four centimeters.

9. The range shifting device of claim 1, wherein the helmet is configured to engage a head frame.

10. The range shifting device of claim 1, wherein the helmet further comprises a hollow frame and at least one insert comprised of the range shifting material, wherein the hollow frame comprises at least one aperture configured to receive the at least one insert.

11. The range shifting device of claim 10, wherein the at least one insert comprises a plurality of inserts and the at least one aperture comprises a plurality of apertures, wherein a portion of the plurality of apertures are configured to receive a portion of the plurality of inserts.

12. The range shifting device of claim 11, wherein the at least one aperture secures the at least one insert within the at least one aperture through a groove and tab configuration.

13. A range shifting helmet for use in radiation beam treatment of a shallow target within a portion of a head of a patient, the range shifting helmet comprising:
  a. range shifting material configured to lower energy of the radiation beam treatment to accommodate Bragg Peak conditions for the shallow target and have a density configured to have high proton stopping power, wherein the range shifting material is positioned proximate the outer surface of the head of the patient to reduce the distance between the skin entry point and the range shifting material;
  b. a hemispherical dome including the range shifting material; and
  c. a cylindrical extension configured to engage a head frame used to support the head of the patient, wherein the cylindrical extension is positioned at a bottom portion of the hemispherical dome of the range shifting helmet.

14. The range shifting helmet of claim 13, wherein the hemispherical dome further comprises:
  i. a hollow frame comprising at least one aperture; and
  ii. at least one insert, wherein the insert includes the range shifting material, wherein the at least one aperture is configured to retain the at least one insert.

15. The range shifting helmet of claim 13, wherein the hemispherical dome is formed from the range shifting material.

16. The range shifting helmet of claim 13, wherein the range shifting material has a thickness that ensures the radiation beam treatment includes a minimal entrance dose and virtually absent exit dose at the shallow target.

17. The range shifting helmet of claim 13, wherein the range shifting material has an effective atomic number of seven.

18. A radiation beam system for the treatment of a shallow target within a head of a patient, the radiation beam system comprising:
  a. a radiation beam source;
  b. a head frame to secure the head of the patient; and
  c. a range shifting helmet positioned between the radiation beam source and the shallow target, the range shifting helmet configured to reduce the distance between an entry point of the radiation beam and the range shifting helmet, the range shifting helmet comprising:
    i. range shifting material comprising:
      A. a density configured to have high proton stopping power; and
      B. a thickness to ensure the radiation beam treatment includes a minimal entrance dose and absent exit dose at the shallow target; and
    ii. a cylindrical extension configured to engage the head frame.

19. The radiation beam system of claim 18, wherein the range shifting helmet further comprises at least one insert and a hollow frame, wherein the hollow frame comprises at least one aperture configured to retain the at least one insert, wherein the at least one insert is formed from the range shifting material.

* * * * *